United States Patent
Cohn (10) Patent No.: US 12,097,137 B2
(45) Date of Patent: Sep. 24, 2024

(54) SYSTEMS AND METHODS FOR INTRAVASCULAR PROCEDURES

(71) Applicant: Michael C. Cohn, Southwest Ranches, FL (US)

(72) Inventor: Michael C. Cohn, Southwest Ranches, FL (US)

( * ) Notice: Subject to any disclaimer, the term of this patent is extended or adjusted under 35 U.S.C. 154(b) by 0 days.

(21) Appl. No.: 18/135,368

(22) Filed: Apr. 17, 2023

(65) Prior Publication Data

US 2023/0248557 A1  Aug. 10, 2023

Related U.S. Application Data

(63) Continuation-in-part of application No. PCT/US2022/011737, filed on Jan. 8, 2022.

(60) Provisional application No. 63/135,598, filed on Jan. 9, 2021.

(51) Int. Cl.
A61F 2/958 (2013.01)
A61F 2/95 (2013.01)
A61F 2/954 (2013.01)

(52) U.S. Cl.
CPC ............ A61F 2/9517 (2020.05); A61F 2/954 (2013.01)

(58) Field of Classification Search
CPC .. A61F 2/95; A61F 2002/9511; A61F 2/9517; A61F 2/9522; A61F 2002/9534; A61F 2/958; A61F 2/962
USPC ........................................................ 606/1, 7
See application file for complete search history.

(56) References Cited

U.S. PATENT DOCUMENTS

| | | | | |
|---|---|---|---|---|
| 6,352,561 B1 * | 3/2002 | Leopold | ................... | A61F 2/07 623/1.11 |
| 6,645,239 B1 * | 11/2003 | Park | ......................... | A61F 2/95 623/1.22 |
| 6,776,791 B1 * | 8/2004 | Stallings | ................... | A61F 2/95 623/1.11 |
| 8,968,379 B2 * | 3/2015 | Pryor | ................ | A61M 25/0136 623/1.11 |
| 10,806,615 B2 * | 10/2020 | Arnault De La Menardiere | ........ | A61F 2/954 |
| 11,510,795 B2 * | 11/2022 | Arnault De La Menardiere | ........ | A61F 2/954 |
| 2007/0270937 A1 * | 11/2007 | Leanna | ..................... | A61F 2/95 623/1.12 |
| 2015/0173923 A1 * | 6/2015 | Mayberry | ............... | A61F 2/954 623/1.11 |
| 2016/0331383 A1 * | 11/2016 | Hebert | ............. | A61B 17/12145 |
| 2018/0071492 A1 * | 3/2018 | Laby | ................. | A61M 25/0155 |

* cited by examiner

*Primary Examiner* — Ahmed M Farah

(57) ABSTRACT

The present invention relates to methods and systems for performing intravascular procedures. More particularly the present invention relates to a vascular treatment system that includes an elongate catheter having a configurable segment with a coaxial expandable member, an expandable ring fastener mounted on the expandable member and a handle assembly connected to the catheter that actuates the configurable segment to change shape and maintain that shape during deployment of the expandable ring fastener within the lumen of a previously placed endovascular graft to secure the graft to a vessel wall.

19 Claims, 13 Drawing Sheets

SYSTEMS AND METHODS FOR INTRAVASCULAR PROCEDURES

BACKGROUND OF THE INVENTION

For many years catheters have been used within the vasculature for diagnostics and therapeutic purposes. In particular balloon catheters have been routinely used for dilatation of stensoses, as well as the delivery of expandable stents to a desired treatment location. To access a particular site within the body, a physician typically directs the catheter through the vasculature using a shaped guide wire to aid in super selecting specific branching vessels until the target site is reached.

Once at the target site, the stent is positioned and the balloon is inflated to expand the stent at the target location. The balloon is then deflated and the catheter is subsequently removed leaving the deployed stent at the target location. Difficulties occur when the treatment site is located in more tortuous or curved anatomy. The inflation of the balloon and subsequent deployment of the stent in curved vessels can cause a straightening of the vessel at the target location leading to hemodynamic changes and ensuing complications including thrombosis. Similarly, endovascular stent grafts may be difficult to position in tortuous anatomy and when treating abdominal aortic aneurysms this difficulty can result in incomplete engagement of the graft with the vessel wall creating a leak path leading to the aneurysm. These leak paths, also known as "endoleaks" create an increased risk for the aneurysm to rupture.

While catheters typically have a primary lumen used for guide wire access and the delivery of therapeutics or contrast media, specialized balloon catheters used for stent delivery typically include an additional lumen to facilitate balloon inflation and stent expansion, steerable catheters typically have multiple lumens. Many examples of steerable catheter exist some of which are described in U.S. Pat. No. 6,945,956 to Waldhauser et al., entitled "Steerable Catheter", U.S. Pat. No. 6,183,435 to Bumbalough et al., entitled "Multi-Directional Steerable Catheters and Control Handles." One example design shown in the "Bumbalough" patent uses "puller wires", which extend from a handle to distal ends anchored in the tip section of the catheter although this design does not have a through lumen. Steerable catheters are designed to aid in accessing the target location to so that a subsequent therapy may be performed.

There is a need for a deployment system in which an expandable device can be placed in a curve vessel and be deployed without straightening the vessel. Additionally, there is a need for fastener system that can be positioned within a previously deployed graft, properly oriented (under imaging (fluoroscopic, ultrasonic, magenetic resonance or the like, as examples)) and deploy a fastener that can engage the graft and secure it to the vessel wall to seal an endoleak.

SUMMARY

In accordance with one aspect there is provided a treatment system for delivering and deploying an expandable implant in a body lumen of a mammal. More particularly, there is provided a vascular treatment system which includes an elongate catheter having a proximal end coupled to a handle assembly, a distal end, with proximal, intermediate and distal sections positioned between the proximal end and distal end, a configurable segment positioned in the distal section, an expandable member positioned around the configurable segment and an expandable implant mounted on the expandable member. The elongate catheter is constructed having a catheter shaft with multiple lumens where a primary through lumen is surrounded by multiple control lumens. Positioned within each of the control lumens is an elongate control wire where the distal end of each control wire is secured in each control lumen at the distal end of the configurable segment and the proximal end of each control wire is secured to an operable member of the handle assembly, such that operation of the operable member in one direction advances the control wire in one control lumen placing it in compression while simultaneously retracting the control wire in an opposing control lumen placing it in tension, which causes the configurable segment to bend or curve. The handle assembly includes a locking member which can restrict movement of the operable member to maintain the configurable segment in a curved configuration. The handle assembly may include additional operable members and locking members when utilizing additional control wires to allow the configurable segment to be placed and maintained in a complex curved configuration. When the treatment system is positioned at a target location in the body, the handle assembly can be operated to place the configurable segment in desired curved configuration. In this curved configuration the expandable member is then expanded causing the expandable implant to expand at the target location in the curved configuration.

In accordance with another aspect there is provided a vascular treatment system where the expandable member takes the form of a balloon and the expandable implant takes the form of an expandable stent. The elongate catheter includes a balloon inflation lumen that extends from a balloon inflation port coupled to the handle assembly through the catheter shaft to the balloon, such that the balloon inflation port is in fluid communication with the balloon. To visualize the configurable segment of the balloon catheter under fluoroscopy, radio-opaque markers are positioned on the catheter shaft at the proximal end of the configurable segment and at the distal end of the configurable segment. Additionally, the expandable stent is preferably radio-opaque or includes radiopaque markers to aid in determining the optimal orientation within the vasculature prior to balloon inflation and subsequent deployment of the stent.

In accordance with yet another aspect there is provided a vascular treatment system where the expandable member takes the form of a self-expanding framework, the expandable implant takes the form of a stent and the system includes a retractable elongate sheath. The retractable sheath having proximal and distal ends, a lumen extending there between and the proximal end being positioned adjacent to the handle assembly. The elongate catheter and stent are slidably disposed within the lumen of the retractable sheath whereby the self-expanding framework is constrained in a compressed configuration such that when the distal end of the treatment system is positioned within the vasculature at a target location and the handle has been operated to place the configurable segment in the desired configuration, the sheath may be retracted proximally to allow the self-expanding framework to expand the stent or other implant radially and in the general shape of the configurable segment at the treatment site.

In accordance with still another aspect there is provided a vascular treatment system where the expandable implant takes the form of an anchoring member. The expandable anchoring member is preferably configured to include barbed portions that become prominent as it is radially expanded and deployed. The length of the anchoring member can range from a minimum of about 2 mm, forming a ring structure, to greater than 200 mm forming a tubular structure. The anchoring member functions to aid in securing a previously deployed graft to the wall of a vessel to prevent the graft from migrating. Similarly a graft secured to the wall by the anchor may seal off a defective portion of the vessel as in the case of an abdominal aneurysm or thoracic aneurysm.

In accordance with another aspect, there is provided an expandable ring fastener having a longitudinal length between about 2 mm and about 10 mm and an expanded diameter greater than about 15 mm. The expandable ring fastener may also include tabs or barbs that extend outwardly from the fastener when the fastener is deployed. During fastener deployment, a steerable catheter allows orienting of the ring just below the graft material/native vessel interphase to facilitate fastening of the material to the vessel in a 3D plane. The tabs or barbs of the ring are adapted to engage the inner surface of the graft causing the graft to expand outwardly against the vessel wall thereby eliminating an endoleak (and or preventing the graft from migrating). With sharpened barbs during deployment, the barbs may also pierce the graft wall and anchor into the vessel wall to secure the graft's position while eliminating the endoleak. As can be appreciated such a device structure is typically contrary to a that of a stent because the deployed expanded diameter of the ring fastener is substantially larger than the axial length and stents which are intended to open a vessel typically have a length substantially greater than a deployed diameter. The teachings and commercialization for stent design is that they should have an increased length relative to their diameter which insures that the stent does not rotate along its axial length to cause a blockage within the vessel or migrate to a different location. While the ring fastener structure (having a larger deployed diameter than axial length) may make it susceptible to rotation along its axial length, the tabs or barbs that engage the graft prevent this from occurring.

In accordance with yet another aspect there is provided an expandable ring fastener mounted onto a balloon catheter having a configurable segment whereby catheter whereby the configurable segment reorients the entire ring fastener when the configurable segment is moved from a first configuration to a second configuration allowing the fastener to be properly oriented in 3 dimensional space prior to deployment. The ability to reorient the entire ring fastener is due to having a longitudinal length that is very short which differs from stents which typically have a long longitudinal length such that only a portion of a stent would be able to be reoriented.

In accordance with still yet another aspect there is provided an expandable ring fastener wherein the expanded diameter of the ring fastener is greater than 1.25 times the longitudinal length of the ring fastener. In some instances, the expanded diameter may be greater than 1.5 times the longitudinal length of the ring fastener. In other instances the expanded diameter may be greater than 2 times the longitudinal length of the ring fastener. In still other instances the ring fastener may have an expanded diameter greater than 2.25 times the longitudinal length. In yet still other instances the ring fastener may have an expanded diameter greater than 2.5 times the longitudinal length of the fastener. In still some other instances, the expanded diameter may be greater than 5 times the longitudinal length of the fastener. The aforementioned dimensional constraints are not aesthetic, but functional to allow the entire fastener to be properly positioned and oriented in 3D space within the graft (and/or vessel interphase), prior to deployment within the graft to insure that the graft is secure to the vessel in the appropriate location.

In accordance with another aspect there is provided a vascular treatment system catheter assembly, expandable member and expandable implant are formed of biocompatible resilient materials. Suitable resilient materials include metal alloys such as nitinol, titanium, stainless steel and cobalt chromium and any alloys thereof. Additional suitable materials include polymers such as polyimides, polyolefins, polyamides, fluoropolymers, polyetheretherketone (PEEK), polyurethanes, EPTFE, polyesters and shape memory polymers. Suitable high tensile strength materials for control wires include metallic wires, cables, fibers or strands of UHMWPE, Kevlar and combinations thereof. Suitable radio-opaque materials include gold, platinum, tungsten, tantalum, iridium and any combinations of alloys thereof. These materials may be formed into desired shapes by a variety of methods which are appropriate to the materials being utilized and components and assemblies being formed such as extrusion, blow molding, laser cutting, injection molding, electro-plating, welding, gluing, electrochemical machining, machining, photo-etching, sputter deposition and casting.

In accordance with another aspect there is provided a method for performing an intravascular procedure using a vascular treatment system. The method includes the steps of:
providing an elongate catheter having distal and proximal ends, a configurable segment positioned proximal the catheter distal end, an expandable member disposed about the configurable segment, an expandable implant positioned on the expandable member and an operable lockable handle assembly coupled to the proximal end of the catheter whereby operation of the lockable handle assembly causes the configurable segment to change shape and when locked to maintain that shape during deployment of the expandable implant;
advancing the distal end of the catheter within a vessel lumen adjacent a target treatment site;
positioning the catheter and expandable implant within the lumen of a previously deployed endovascular graft.
operating the handle assembly to change the shape of the configurable segment;
positioning the configurable segment and expandable implant in a desired orientation;
operating the handle assembly to lock the configurable segment in the curved configuration;
expanding the expandable member while the configurable segment is locked in the curved configuration to thereby expand the expandable implant at the treatment site while in the curved configuration;
condensing the expandable member to thereby disengage from the expandable implant;
withdrawing the catheter from the vasculature.

DETAILED DESCRIPTION

Figure 1A:
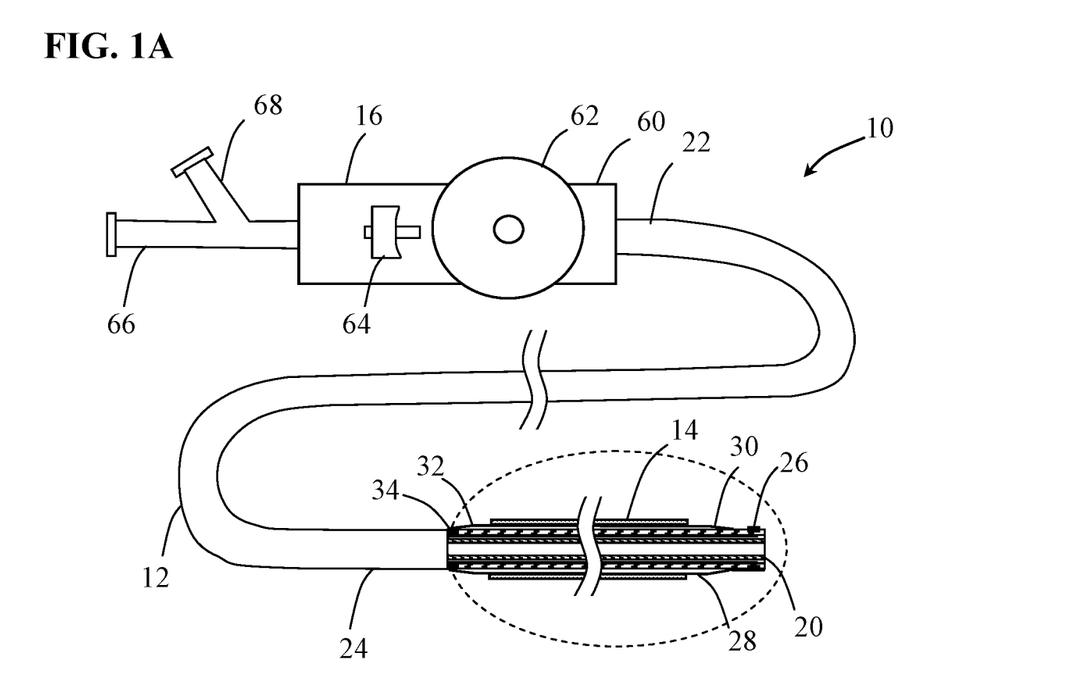
FIG. 1A is a partial cross-sectional view of a vascular treatment system for deploying an expandable implant including a steerable balloon catheter.
Figure 1B:
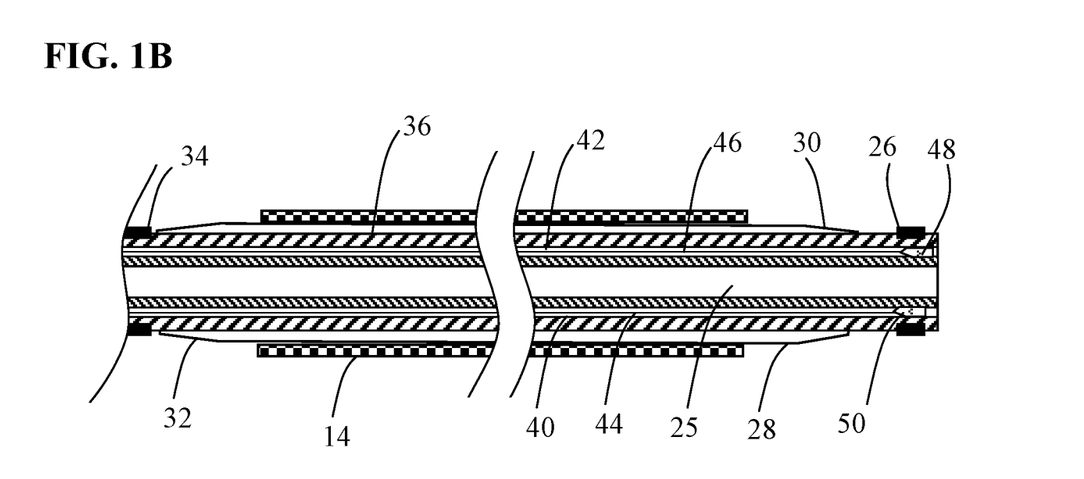
FIG. 1B is an enlarged partial cross-sectional view of the distal end of the catheter.

Methods and systems for treating vascular defects within the body are herein described. FIGS. 1A-1B illustrates an embodiment of a vascular treatment system 10. Vascular treatment system 10 includes an elongate catheter 12, a stent 14, and a handle assembly 16. Elongate catheter 12 has a distal end 20, a proximal end 22, an intermediate section 24, a primary through lumen 25 and a radio-opaque marker 26 positioned at the catheter distal end. An inflatable balloon 28 having a distal end 30 and a proximal end 32 is positioned on the catheter distal to the intermediate section 24. Balloon distal end 30 is positioned adjacent marker 26 while proximal end 32 is positioned distally adjacent proximal radio-opaque marker 34. Balloon 28 is positioned on catheter 12 coincident with the catheter configurable segment 36. Elongate catheter 12 has a steerable construction that includes multiple control wire lumens 40 and 42 that extend from the catheter's proximal end to the distal end. Disposed within each the control wire lumens 40 and 42 are high strength control wires 44 and 46 respectively. Control wires 44 and 46 have distal ends that are secured within their respective control wire lumens adjacent the catheter distal end 20 with securing members 48 and 50, respectively. The securing members preferably takes the form of a high strength UV curable adhesive that maintain the control wires connection to the catheter when placed under high tensile and compressive load. The proximal ends of the control wires extend to and are coupled to handle assembly 16. Handle assembly 16 includes a housing member 60, a directional wheel 62, a locking brake 64, a primary lumen hub 66 and a balloon inflation port 68. The primary lumen hub 66 is in direct communication with primary lumen 25 to allow guide wire access, the delivery of therapeutics or contrast media. The balloon inflation port 68 is in fluid communication with balloon 28 such that operation of a fluid filled syringe coupled to the port causes the balloon 28 to expand. The directional wheel 62 operates to place the configurable segment 36 in a curved configuration. Locking brake 64 is shown in the form of a slidable member that can be operated to engage the directional wheel 62 to thereby "lock in" the curved configuration of the configurable segment 36. As can be appreciated the locking brake or locking member may take any suitable engineered form that secures the configurable segment in the curved configuration.

Figure 2A:
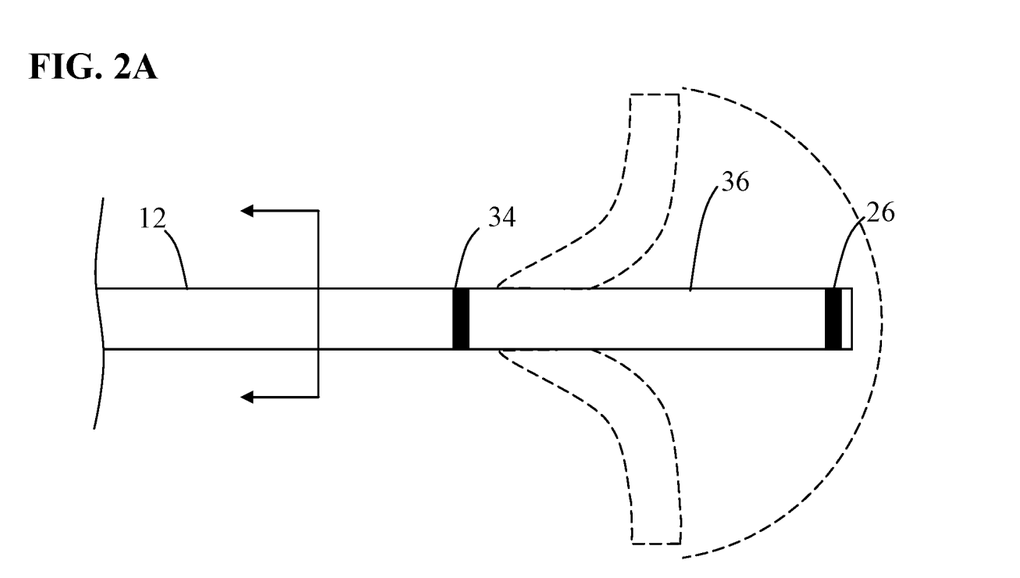
FIG. 2A is a side view of the catheter distal portion showing the configurable segment in bending configurations.

FIG. 2A shows configurable segment 36 of catheter 12 in a neutral general straight passive configuration and the potential bending of the segment when operated by wheel 62. As previously discussed, the proximal ends of the control wires are coupled to the handle assembly 16, but more particularly, the proximal ends of the control wires are arranged and fixedly attached to the directional wheel 62, such that rotation of the wheel in a first direction causes the control wire in one control lumen to advance distally placing it under a compressive load, while a control wire in a separate control lumen is retracted placing it under a tensile load which in turn causes the configurable segment 36 to bend or curve in a first direction. When the directional wheel 62 is rotated in the opposite direction the aforementioned loads on the control wires reverse causing the configurable segment 36 to bend or curve in a direction opposite to the first direction. This allows the configurable segment 36 to have 180 degrees of bending in a plane. Of course the entire catheter shaft can be somewhat rotated to aid in orienting the configurable segment in a desired position.

Figure 2B:
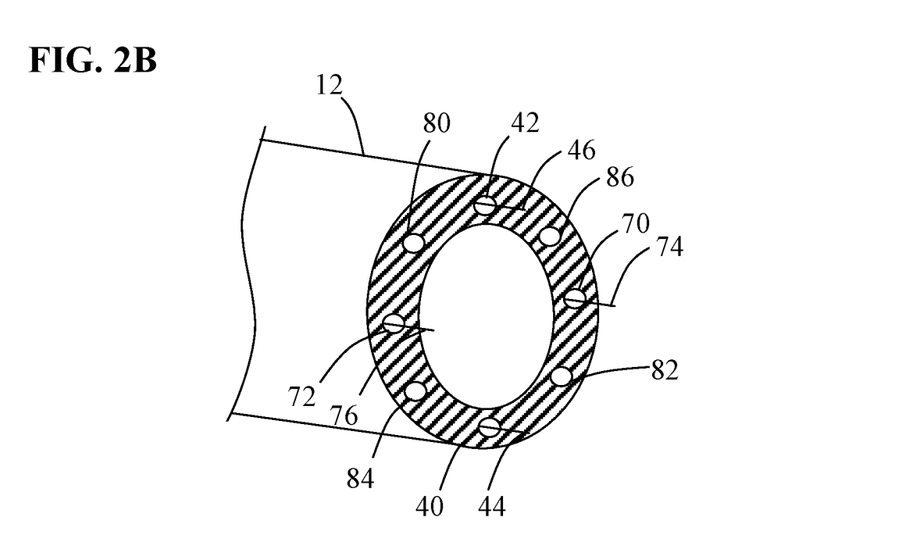
FIG. 2B is a partial cross section of the catheter shown in FIG. 2A.
Figure 3A:
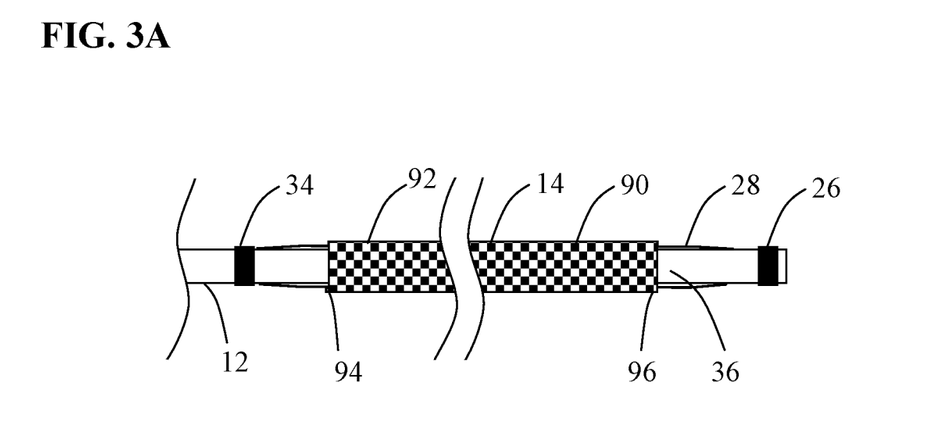
FIGS. 3A-3E are side views of the distal portion of the treatment system shown in FIG. 1 depicting the steps to deploy the stent implant.
Figure 3B:
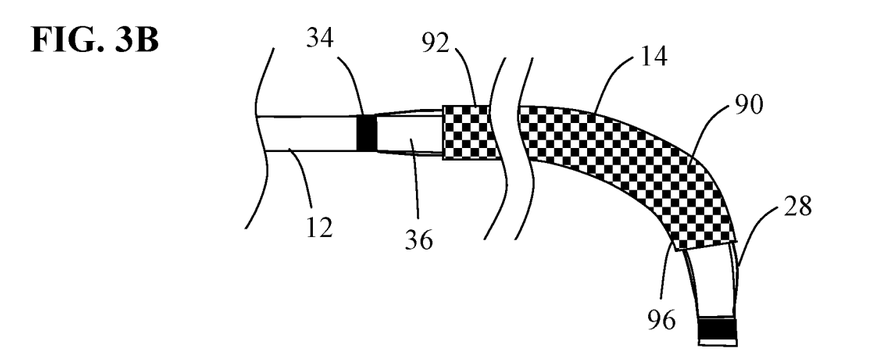
Figure 3C:
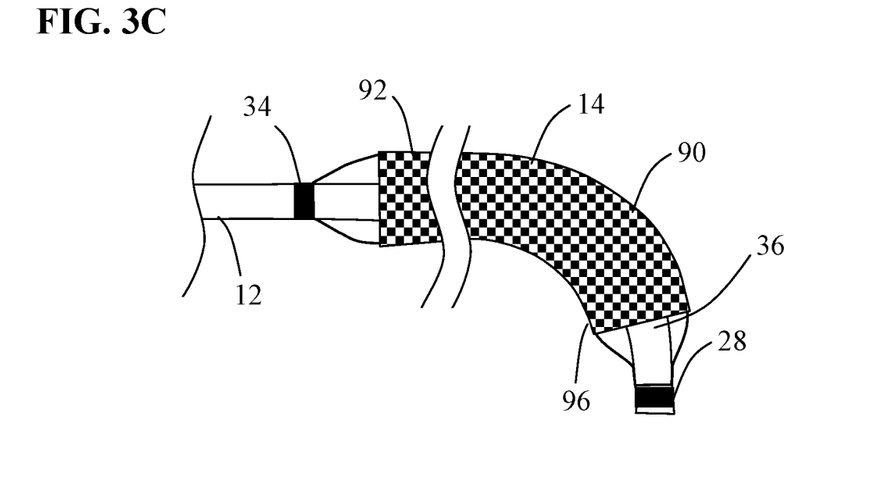
Figure 3D:
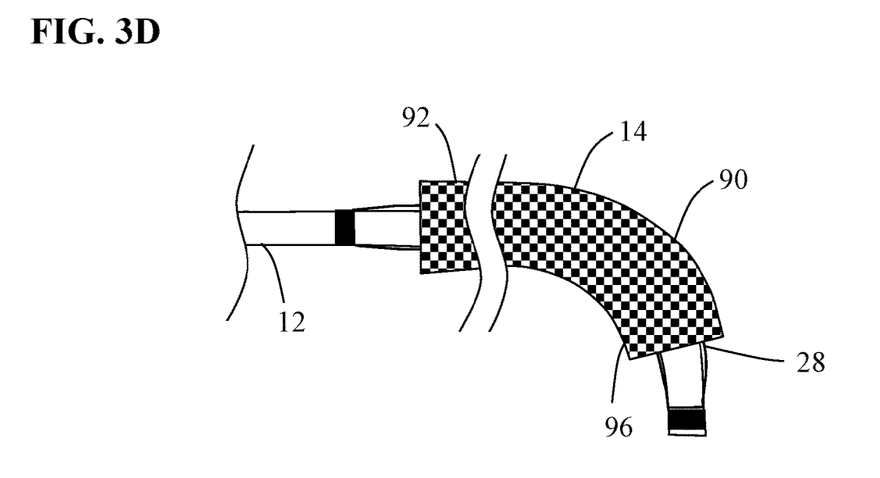
Figure 3E:
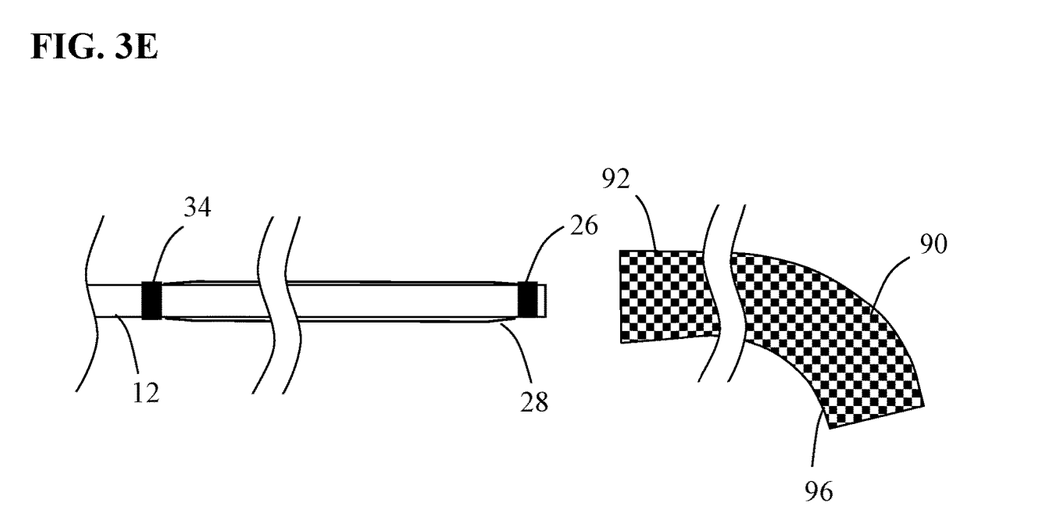
Figure 4A:
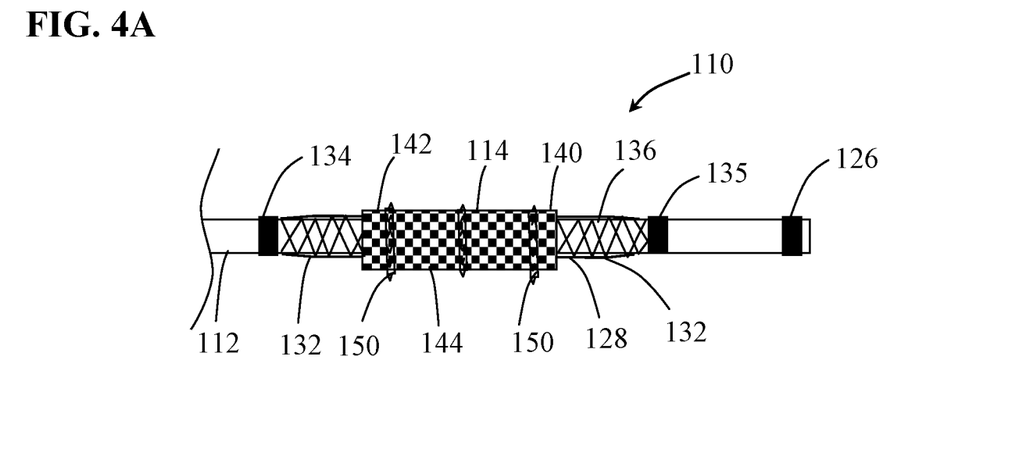
FIGS. 4A-4D are side views of the distal portion of a modified vascular treatment system depicting the steps to deploy an anchor implant.
Figure 4B:
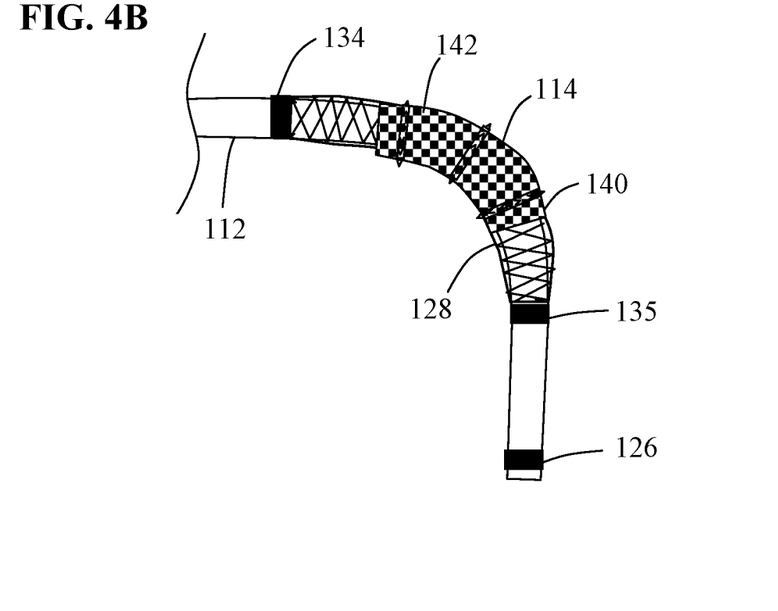
Figure 4C:
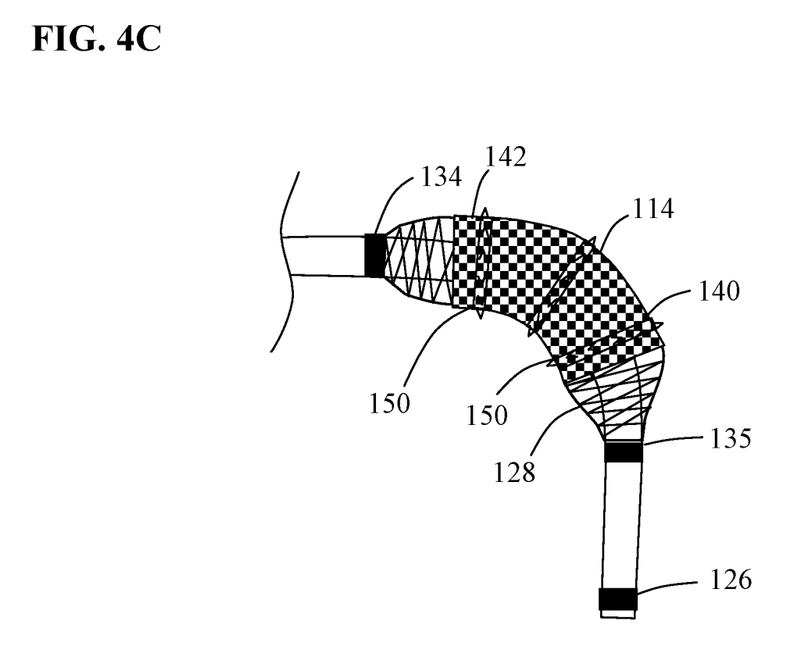
Figure 4D:
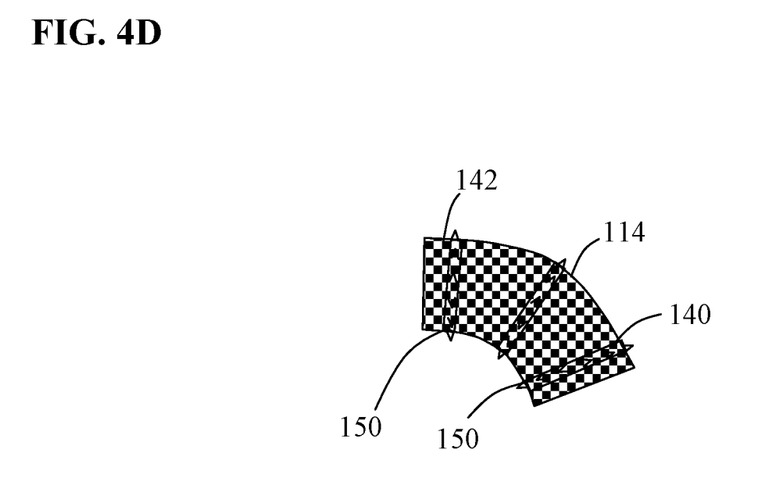
Figure 5A:
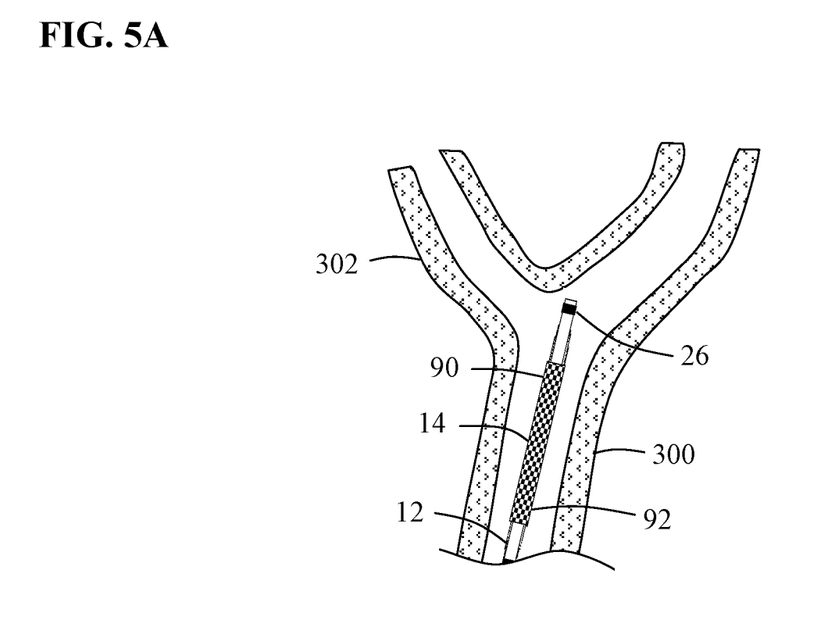
FIGS. 5A-5D are side views of the distal portion of the treatment system shown in FIG. 1 depicting the steps to deploy the stent implant in the vasculature of a mammal.
Figure 5B:
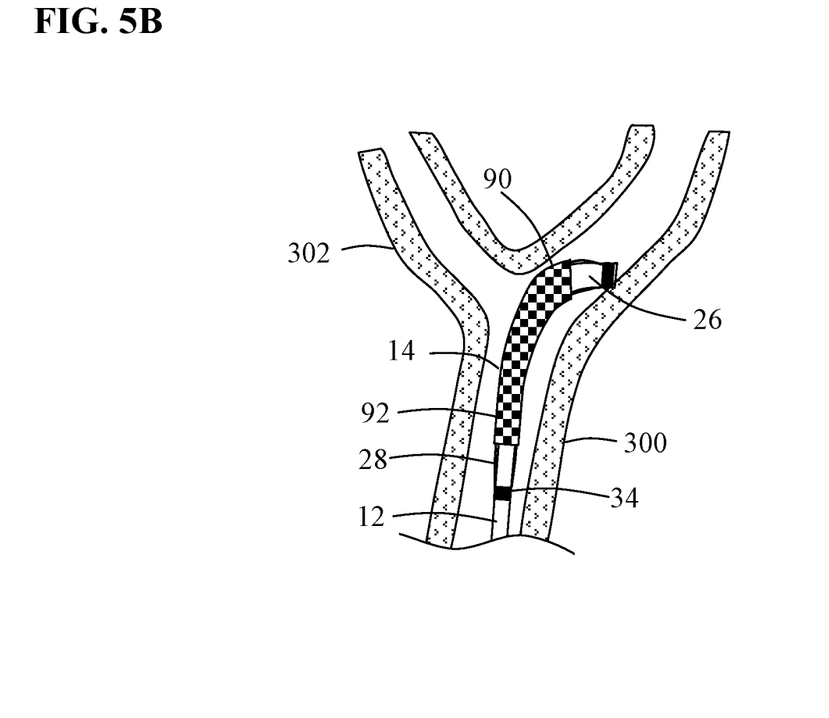
Figure 5C:
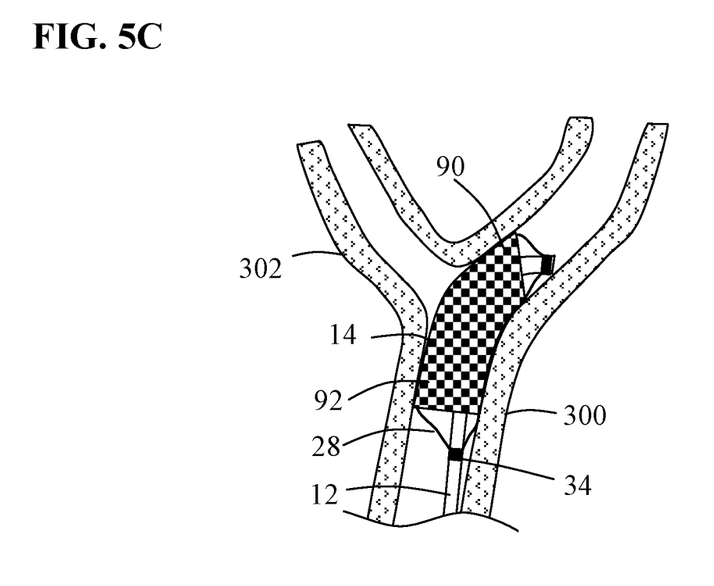
Figure 5D:
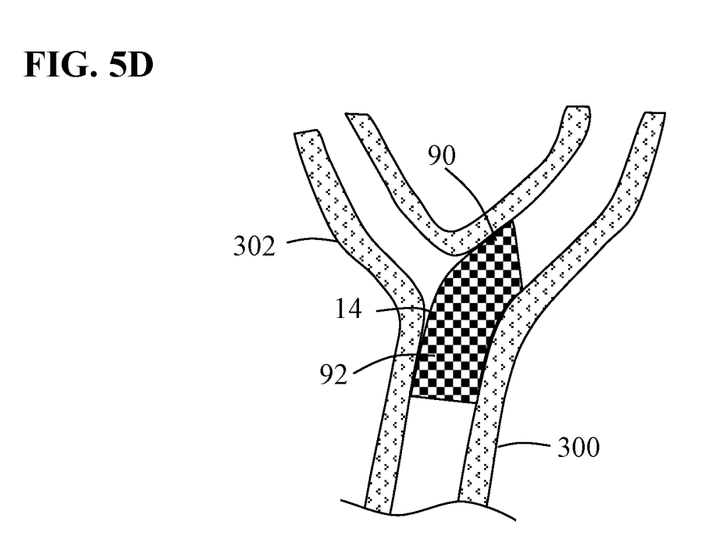

A cross section of catheter 12 is shown in FIG. 2B illustrating a catheter shaft having a primary lumen 25 and multiple smaller lumens. Additional control wire lumens 70 and 72 respectively are shown with additional control wires 74 and 76 respectively positioned within the lumens. These control wires have distal ends that are similarly secured within their respective control lumens adjacent to the catheter distal end 20. The proximal ends of the control wires are coupled to handle assembly 16, arranged and fixedly attached to a second directional wheel (not shown), such that rotation of the second wheel in a first direction causes the control wire in one control lumen to advance distally placing it under a compressive load, while a control wire in a separate control lumen is retracted placing it under a tensile load which in turn causes the configurable segment 36 to bend or curve in a first direction. When the second directional wheel is rotated in the opposite direction the aforementioned loads on the control wires reverse causing the configurable segment 36 to bend or curve in a direction opposite to the first direction. The use of a second directional wheel (and associated locking brake not shown) and the additional control wires allows the configurable segment 36 to have 180 degrees of bending in multiple planes without having to rotate the catheter. Balloon inflation lumens 80 and 82 are shown which are sealed distal to the balloon but have openings that access the interior of balloon 28. The proximal ends of the inflation lumens are coupled to balloon inflation port 68 such that the port is in fluid communication with interior of balloon 28. Additional auxiliary lumens 84 and 86 may be present that could be used for inflation or additional control wires.

FIGS. 3A-3E shows the basic steps of operating vascular treatment system 10 to deploy a stent, stent segment or stent graft. Vascular treatment system 10 is shown with stent 14 mounted on catheter 12. More particularly, stent 14 is positioned on balloon 28. Stent 14 has a distal portion 90, a proximal portion 92 and distal and proximal ends 94 and 96 respectively. Operating the handle assembly, places the configurable segment in an active curved configuration while also curving stent 14. Locking brakes are engaged to maintain the configurable segment in the curved configuration. A fluid filled syringe is then coupled to the balloon inflation port 68. Injection of fluid causes the expansion of balloon 28 that also expands stent 14. The "locked in" curved configuration of the configurable segment guides the balloon 28 and the stent 14 to expand in the shape of the curved configurable segment. The high tensile strength control wires and securing members allows the configurable segment to be maintained in the curved configuration during balloon expansion which generates high forces as the balloon attempts to straighten. The forces placed on the control wires are substantially higher than forces encountered in regular steerable catheters because regular steerable catheters are only designed to deflect a catheter tip to aid in vascular navigation. Once stent 14 has been sufficiently expanded, balloon 28 is then deflated by withdrawing fluid from the balloon back into the syringe. The plastic deformation of the stent during the expansion process maintains the stent in the curved configuration of the configurable segment. The locking brakes are then disengaged allowing catheter 12 to be retracted from the deployed stent 14.

The basic operation of an alternate configuration of a vascular treatment system is shown in FIGS. 4A-4D to deploy an expandable anchor. Vascular treatment system 110 includes an elongate catheter 112, an expandable anchor 114 mounted on the catheter and a handle assembly similar to the handle assembly of treatment system 10. Treatment system 110 also includes a retractable/advance able sheath 116 (not shown) disposed about catheter 112 and mounted anchor 114. Catheter 112 has a radio-opaque marker 126 positioned at the distal end of the catheter. Catheter 112 has a self-expanding framework 128 positioned proximal to the catheter distal end. Framework 128 has a distal end 130 and a proximal end 132 both of which are fixedly secured to the catheter. Catheter 112 has similar control lumen and control wire construction to catheter 12 except that distal ends of the control wires are secured proximal to marker 126 and distal to distal end 130 of the self-expanding framework 128. A proximal catheter marker 134 is positioned proximal to framework proximal end 132 and an intermediate marker 135 is positioned distal to the framework distal end 130. The proximal and intermediate markers 134 and 135 respectively, visually define the configurable segment 136. The anchor 114 is mounted on the self-expanding framework 128 in a compressed configuration which is maintained by retractable sheath 116 (not shown). Anchor 114 has a distal portion 140, a proximal portion 142 and an intermediate portion 144. The anchor 114 is preferably constructed to include a plurality of barbs 150 that extend when the anchor is in an expanded configuration. The anchor is used to secure previously placed grafts into an appropriate position within the vasculature to prevent the graft from migrating or aid in sealing the graft against the vessel to exclude defects, like an aneurysm. The anchor may take the form of an expandable ring or framework having an axial length of about 2 to 10 mm, more preferably 2 to 5 mm or tubular shape having a length (substantially less than the length of the graft) appropriate to secure the intended graft locations. It is important to note that the short length of the anchor make them unsuitable for use as a stent for opening vessel, especially in the case of treating abdominal or thoracic aneurysms.

Operating vascular treatment system 110 begins by operating the handle assembly, which places the configurable segment 136 in an active curved configuration while also curving anchor 114 and sheath 116 (not shown). Locking brakes are engaged to maintain the configurable segment in the curved configuration. Retraction of the retractable sheath 116 allows self-expanding framework 128 to expand that also expands the anchor 114. The "locked in" curved configuration of the configurable segment guides the framework 128 and the anchor 114 to expand in the shape of the curved configurable segment. The high tensile strength control wires and securing members allows the configurable segment to be maintained in the curved configuration during framework expansion which generates high forces as the framework attempts to straighten. Once anchor 114 has been sufficiently expanded, sheath 116 (not shown) is advanced distally over catheter 112 causing framework 128 to move to a compressed configuration. The plastic deformation of the anchor during the expansion process maintains the anchor in the curved configuration of the configurable segment. The locking brakes are then disengaged allowing catheter 112 to be retracted from the deployed anchor 114.

FIGS. 5A-5D illustrate the method steps to perform an intravascular procedure using a vascular treatment system to deploy a stent, stent segment, stent anchor or graft. Vascular treatment system 10 is shown with stent 14 mounted on catheter 12 positioned on balloon 28. Stent 14 has a distal portion 90, a proximal portion 92 and distal and proximal ends 94 and 96 respectively. Catheter 12 is inserted into the vasculature and navigated to primary vessel 300 which has some degree of curvature. Adjacent vessel 300 is a branch vessel 302. The target location for the stent deployment is in the primary vessel 300 with the deployed stent crossing the ostium of branch vessel 302. Under fluoroscopy, the configurable segment of catheter 12 is navigated to the target area positioned in vessel 300. Operating the handle assembly, places the configurable segment in an active curved configuration while also curving stent 14. Locking brakes are engaged to maintain the configurable segment in the curved configuration. A fluid filled syringe is then coupled to the balloon inflation port 68 and actuated to cause the expansion of balloon 28 also expanding stent 14. The "locked in" curved configuration of the configurable segment guides the balloon 28 and the stent 14 to expand in the shape of the curved configurable segment. As previously discussed, the high tensile strength control wires and securing members allows the configurable segment to be maintained in the curved configuration during balloon expansion which generates high forces as the balloon attempts to straighten. Once stent 14 has been sufficiently expanded, balloon 28 is then deflated by withdrawing fluid from the balloon. With the deployment being constrained by the curved configurable segment the curvature of vessel 302 is unchanged. The plastic deformation of the stent during the expansion process maintains the stent in the curved configuration of the configurable segment. The locking brakes are then disengaged allowing catheter 12 to be retracted from the deployed stent 14. The catheter 12 is then removed from the vasculature.

As can be appreciated the aforementioned described method steps of using the particular vascular treatment system can be modified and used with modified treatment systems where for example the implant mounted on the balloon member is replaced with a lubricious sheath covering an implant mounted on a self-expanding framework. The steps associated with inflating and deflating the balloon may be substituted and be analogous in the modified system to retracting the lubricious sheath allowing the self-expanding member to expand and advancing the lubricious sheath over the self-expanding member to condense or compress the self-expanding member.

Figure 6:
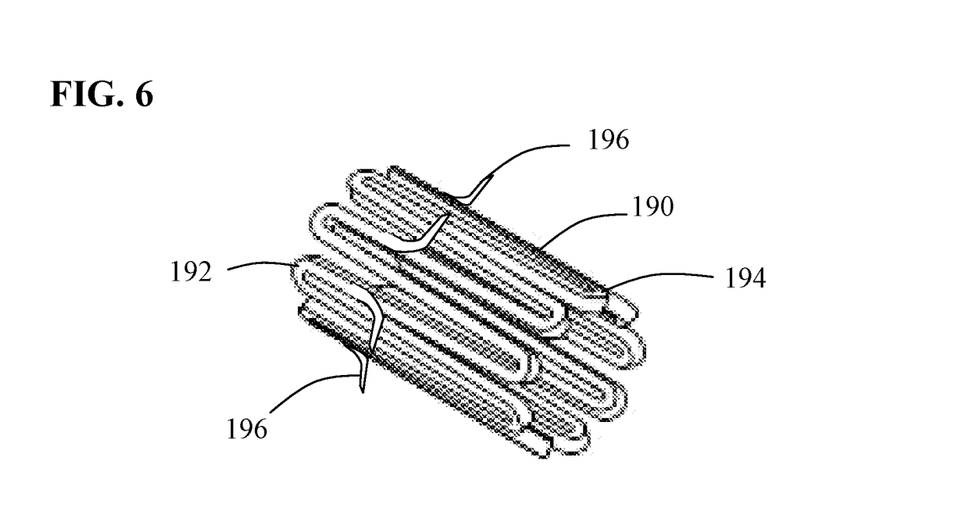
FIG. 6 is perspective view of a preferred embodiment of an expandable ring anchor implant in a collapsed configuration having a plurality of outwardly biased anchor barbs.

FIG. 6 illustrates a preferred embodiment of an expandable ring implant 190 for use in securing vascular implants previously placed in the vasculature. The ring implant 190 is formed using materials and methods known in the art used for stent manufacturing (including self-expanding and balloon expandable). The ring implant has a generally tubular or cylindrical structure and is shown in a collapsed configuration having a plurality of folds of a primary contiguous strut. This configuration may be laser cut from a tube, made by folding or other forming techniques including wire forming. Other means of manufacturing the implant including etching my also be suitable. Ring implant 190 has first and second ends 192 and 194 respectively. In a preferred embodiment the ring implant 190 includes a plurality of barb members 196, radially positioned around the central axis of the cylindrical construct. The ring implant 190 typically has a longitudinal length extending between the first and second ends 192 and 194 and a central axis. The longitudinal length of the ring implant is typically longer in the collapsed configuration than it is when the implant is in the deployed or expanded configuration. The barb members 196 are biased outwardly from the central axis, however the barb members may be oriented in a plane parallel to the central axis when constrained within a sheath. Alternative configurations for barb members may also be suitable, for instance, the implant may include barbs that extend outwardly only upon expansion of the ring implant from its collapsed configuration. While the barbs are shown in ring implant 190 are shown extending near the middle of the axial length, they may also be positioned adjacent the ends of the ends of the implant. The barbs are preferably sharpened so that they may be able to pierce the graft wall and engage the vessel wall. Alternatively the barbs may be blunted, so that when engaging the graft wall they do not pierce the graft but cause the graft to protrude into the vessel wall eliminating the endoleak. The implant may incorporate radio-opaque materials so that the struts and/or barbs may be visible under fluoroscopy to aid in properly orienting the device.

Figure 7:
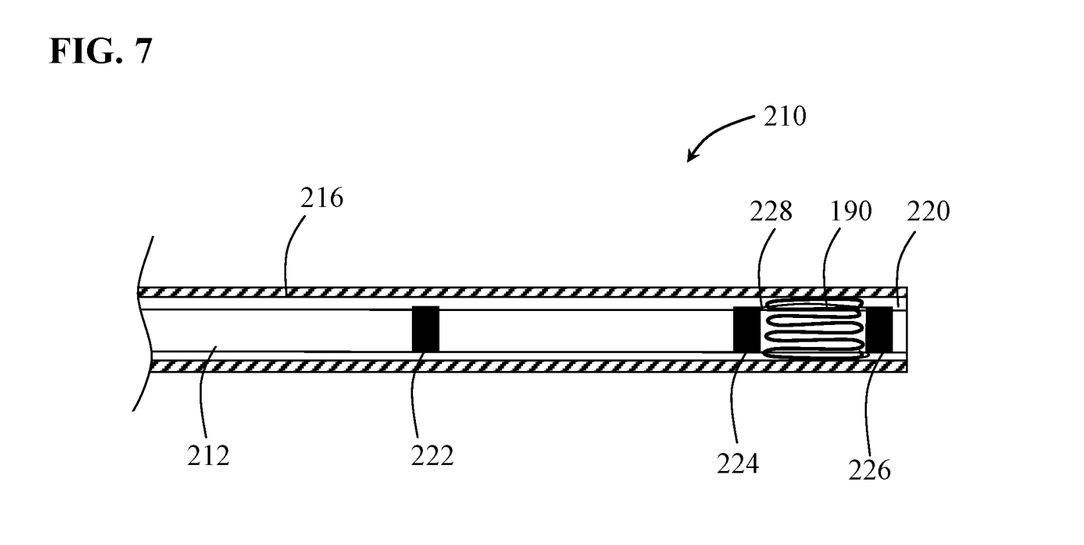
FIG. 7 is a partial cross-sectional view of a vascular treatment system for deploying the implant of FIG. 6 mounted on a steerable balloon catheter.

As shown in FIG. 7, treatment system 210 includes ring implant 190 positioned on a steerable balloon catheter 212, for delivery into the vasculature of a patient. Steerable balloon catheter 212 is constructed similarly to previously described steerable systems having a distal end 220, a proximal marker 222, intermediate marker 224 and a distal marker 226. Balloon 228 is positioned between intermediate maker 224 and distal marker 226. Balloon 228 typically has an axial length that is approximate the length of the ring implant or slightly greater. Ring implant 190 is mounted onto balloon 228 and disposed within slidable sheath 216. Slidable sheath 216 insures that the biased barbs 196 are oriented generally parallel to the central axis for delivery.

Figure 8A:
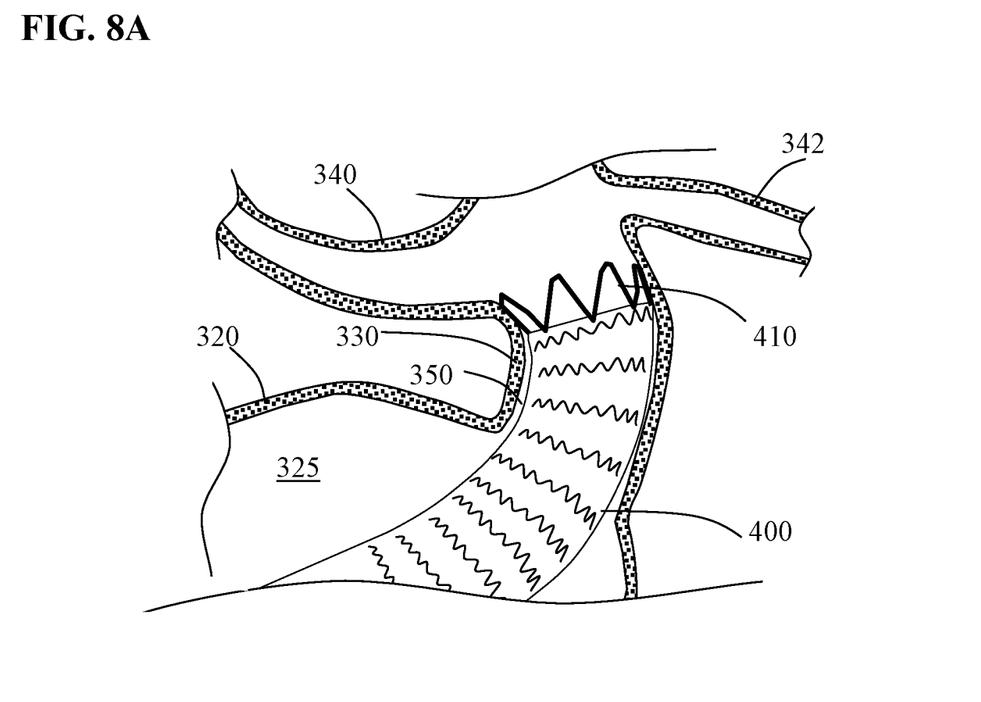
FIGS. 8A-8G are partial sectional views of the vasculature of an abdominal aortic aneurysm treated with a previously placed endovascular graft having an endoleak and the steps to secure the graft to the vessel wall using the system depicted in FIG. 6 and FIG. 7.
Figure 8B:
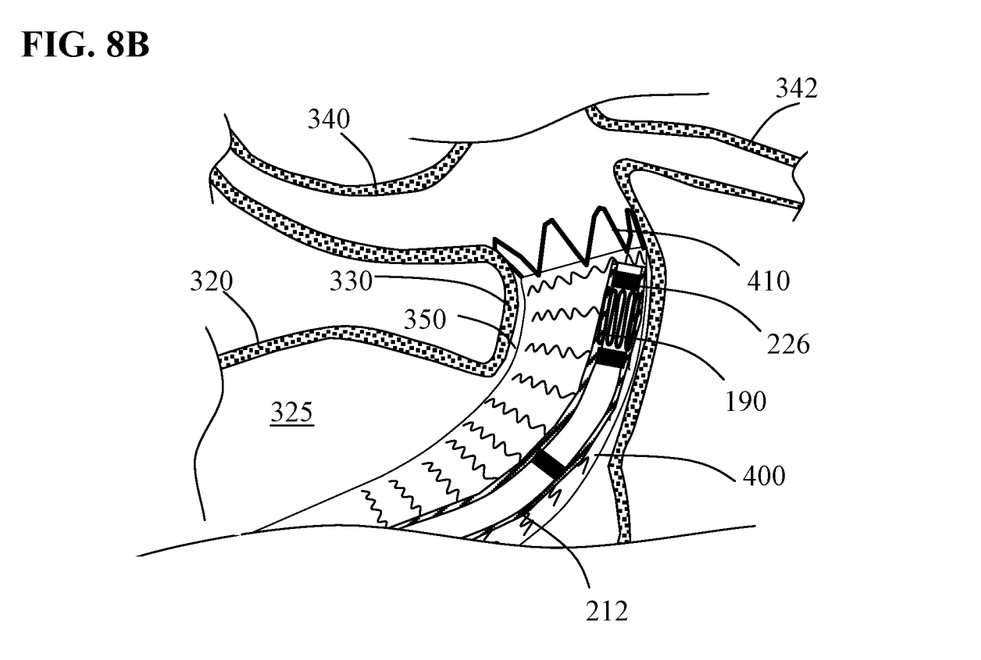
Figure 8C:
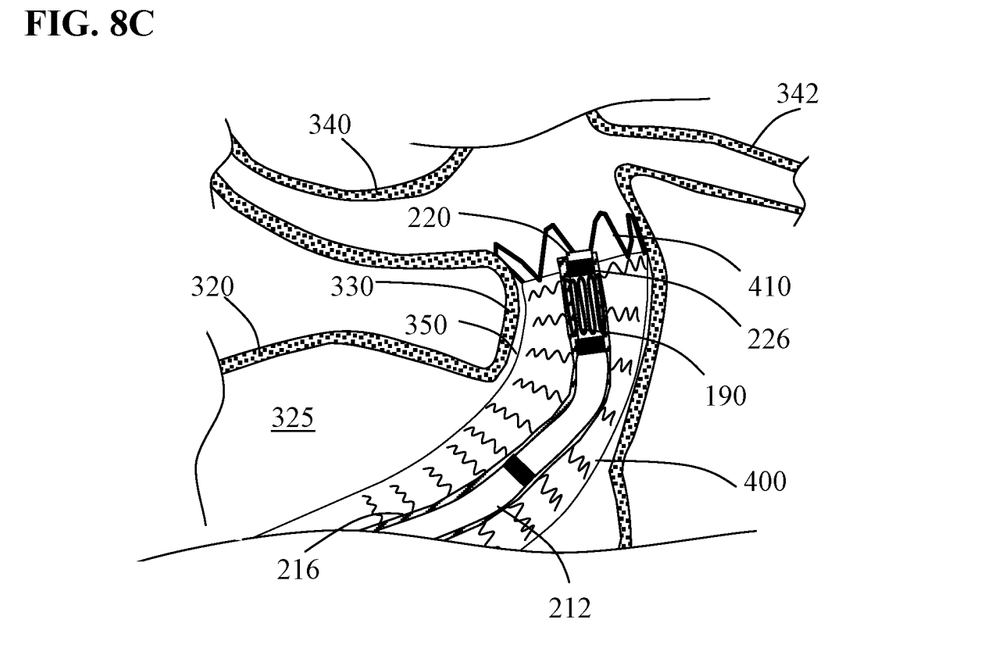
Figure 8D:
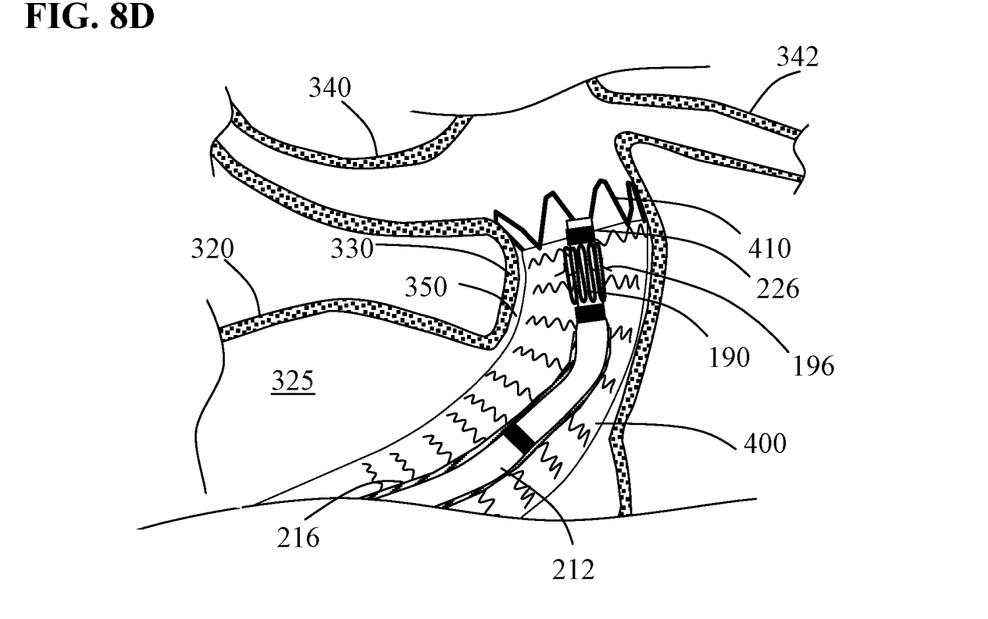
Figure 8E:
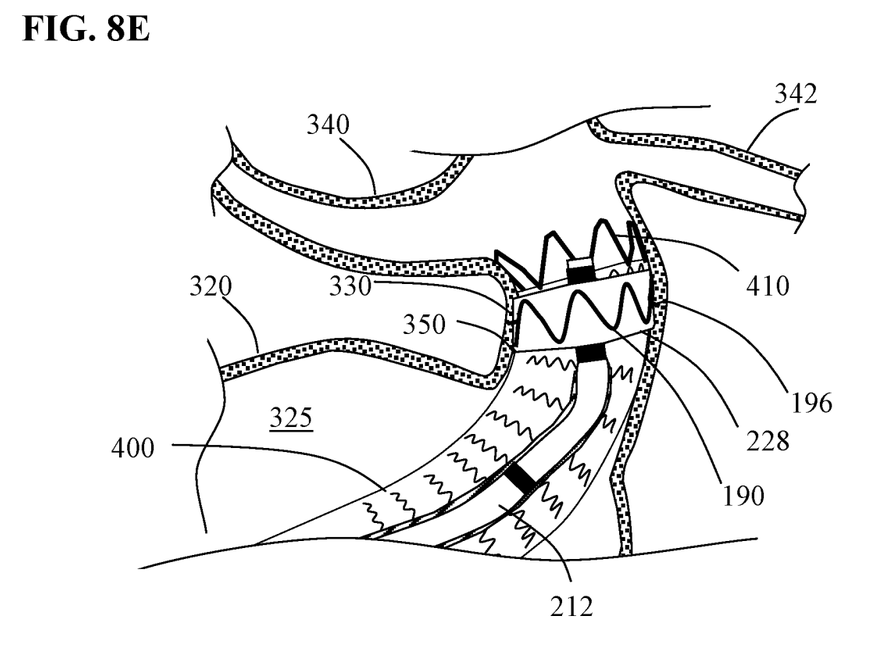
Figure 8F:
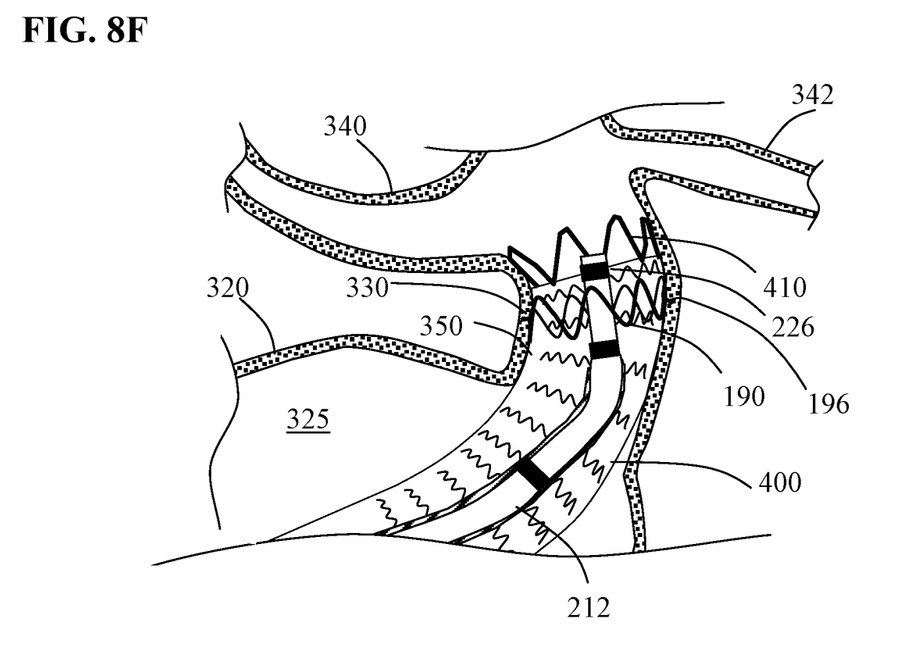
Figure 8G:
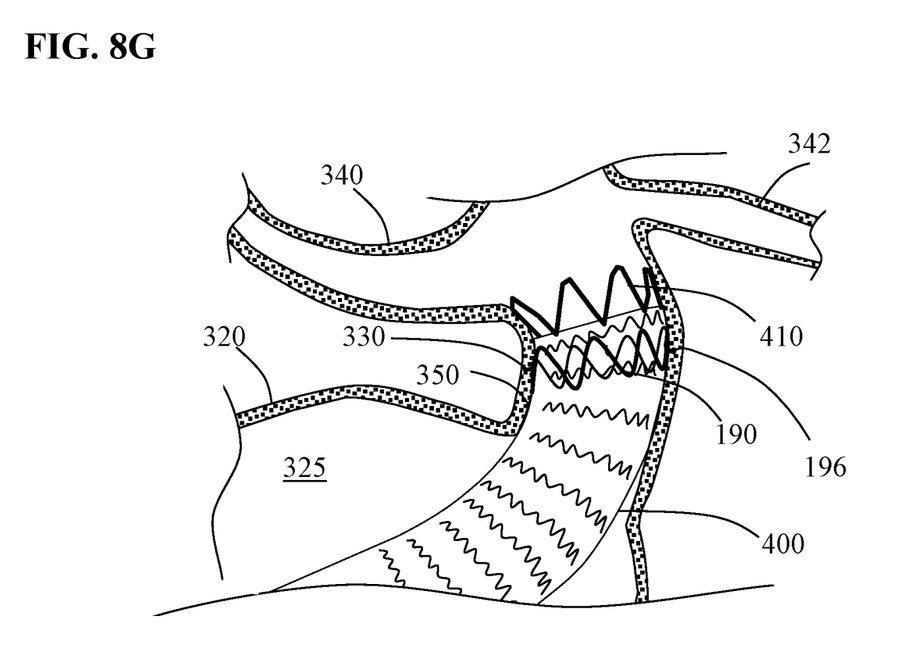

To illustrate the deployment of the treatment system for a particularly difficult to treat vascular anatomy FIGS. 8A through 8G show the vascular associated with an abdominal aortic aneurysm 320 having an aneurysmal sac 325. A previously deployed endovascular graft 400 is shown positioned in the abdominal aorta adjacent wall 330 below the renal arteries 340 and 342. As shown, the graft 400 does not exactly coincide with wall 330, leaving a blood flow path or endoleak 350 from the aorta to the aneurysm sac. Untreated, the abdominal aneurysm is at substantial risk for rupture. The very short distance between the origin of the renal arteries and the aneurysm makes treating this defect properly is extremely difficult. While some physicians have tried to place conventional stents in this location to try and eliminate an endoleak, they have found that the conventional stents are too long (potentially blocking the renal arteries), do not have delivery systems that can precisely place them in the appropriate orientation and position (deploying the stent at a non-beneficial location) and or do not adequately engage the graft (making both structures prone to migration). Similar difficulties have also been noted when treating Thoracic Aneurysms. To repair the endoleak 350 (and also reduce the migration of graft end 410) treatment system 210 is delivered through the vasculature of a patient and into the lumen of graft 400, as depicted in FIG. 8B. As with many flexible catheter systems, the distal end 220 lay adjacent the internal wall of graft 400 near graft end 410. The deployment of ring implant 190 at this position would not be able to adequately secure the graft in place and repair the endoleak and may even cause the graft end 410 to be repositioned such that it occludes a portion of the renal artery leading to complications. With the steerable nature of catheter 212 (and under fluoroscopy) the distal end 220 can be oriented into the proper position shown in FIG. 8C. The catheter can then be locked into a curved position so that sheath 216 can be retracted as in FIG. 8D. Upon retraction of sheath 216, implant 190 is uncovered and barbs 196 extend outwardly. FIG. 8E shows the inflation of balloon 228 and expansion of ring implant 190. Like ring implant 190, balloon 228 typically has an expanded diameter which is substantially larger than axial length of the balloon which differs from stent balloon systems. As the balloon 228 is expanded to a diameter slightly greater than the diameter of graft 400, barbs 196 engage and preferably pierce the wall of graft 400 and engage vessel wall 330. Balloon 228 is then deflated and catheter 212 removed from the graft and patient while leaving the ring implant 190 engaged with the interior of the graft and barbs 196 piercing the graft wall, securing it to the vessel wall, thus removing the blood path into the aneurysm sac and repairing the endoleak 350. Alternatively, barbs 196 may engage the wall of the graft without piercing the graft wall, deforming the graft at the barb locations such that those portions more readily engage the vessel wall to secure the graft and eliminate the endoleak.

Novel devices, systems and methods have been disclosed to perform intravascular procedures. Although preferred embodiments have been described, it should be understood that various modifications including the substitution of elements or components which perform substantially the same function in the same way to achieve substantially the same result may be made by those skilled in the art without departing from the scope of the claims which follow.

What is claimed is:

1. A vascular treatment system comprising:
   an elongate tubular catheter having proximal and distal segments, proximal and distal ends, a lumen extending there between, a shape configurable segment having an axial length positioned proximal to said distal end and an expandable member coincident with a portion of said configurable segment, said configurable segment having a first configuration wherein said configurable segment has a generally straight passive shape and a second configuration wherein said configurable segment has an actively curved shape;
   a handle coupled to the proximal end of said catheter, said handle being operable to move said configurable segment between said first and second configurations;
   a radially expandable ring fastener having a radially expandable framework coupled to a plurality of tacking members extending outwardly from said framework positioned on said catheter, said expandable ring fastener having a delivery configuration wherein said fastener is mounted on the expandable member of said catheter such that when said configurable segment is moved from said first configuration to said second configuration the fastener is oriented at an angle up to about 20 degrees from the oriented angle in said first configuration.

2. A vascular treatment system as in claim 1 wherein said handle includes an operable locking member such that when said configurable segment is in said second configuration and said locking member is operated said configurable segment is maintained in said second configuration.

3. A vascular treatment system as in claim 1 wherein said expandable member is a balloon and said catheter includes an inflation lumen extending from said catheter proximal end to said balloon and said handle includes a port which is in fluid communication with said inflation lumen and balloon.

4. A vascular treatment system as in claim 1 wherein said catheter includes a control wire lumen and a control wire disposed within said control wire lumen, said control wire having a first end fixedly attached to a distal end of said configurable segment and a second end coupled to said handle whereby, operation of said handle applies tension or compression to said control wire thereby causing the configurable segment to change shape.

5. A vascular treatment system as in claim 1 wherein said catheter includes radio-opaque markers positioned distal and proximal to said configurable segment to thereby identify said configurable segment.

6. A vascular treatment system as in claim 1 wherein said expandable ring fastener tacking members includes a plurality of barbs.

7. A vascular treatment system as in claim 6 wherein said barbs are biased outwardly from said fastener when said fastener is expanded.

8. A vascular treatment system as in claim 7 wherein said catheter is slidably disposed in a retractable sheath whereby said sheath constrains said barbs from extending outwardly from said fastener when said fastener is disposed within said sheath.

9. A method of performing an intravascular procedure comprising:
providing a vascular treatment system as claim 1;
positioning the distal end of said catheter within a vessel lumen at a treatment site;
positioning the distal end of said catheter within the lumen of a previously positioned endovascular graft;
orienting said expandable ring fastener within the lumen of the graft;
operating said handle to move said configurable segment from said first configuration to said second configuration;
operating said handle to secure said configurable segment in said second configuration;
expanding said expandable ring fastener and said expandable member while said configurable segment is in said second configuration such that said tacking members engage the wall of the graft;
condensing said expandable member;
removing said catheter from the vasculature.

10. A method of performing an intravascular procedure according to claim 9 wherein said tacking members take the form of barbs and the step of expanding said expandable ring fastener includes the additional step of piercing the wall of said graft with said barbs.

11. A vascular treatment system as in claim 1 wherein said fastener includes an expanded configuration and said framework includes a longitudinal length and a diameter, said fastener being moveable from said delivery configuration to said expanded configuration such that when said framework is positioned within a vascular graft positioned within a vessel and moved from said delivery configuration to said expanded configuration, said tacking members engage the vascular graft thereby securing it to the vessel.

12. A vascular treatment system as in claim 11 wherein said diameter of said framework is greater than said longitudinal length when said fastener is in said expanded configuration.

13. A vascular treatment system as in claim 12 wherein said diameter is greater than 2 times said longitudinal length.

14. A vascular treatment system as in claim 12 wherein said diameter is greater than 5 times said longitudinal length.

15. A vascular treatment system comprising:
an elongate tubular catheter having proximal and distal segments, proximal and distal ends, a lumen extending there between, a shape configurable segment having an axial length positioned proximal to said distal end and an expandable member coincident with a portion of said configurable segment, said configurable segment having a first configuration wherein said configurable segment has a generally straight passive shape and a second configuration wherein said configurable segment has an actively curved shape;
a handle coupled to the proximal end of said catheter, said handle being operable to move said configurable segment between said first and second configurations;
a radially expandable ring fastener having a radially expandable framework coupled to a plurality of tacking members extending outwardly from said framework positioned on said catheter, said expandable ring fastener having a delivery configuration wherein said fastener is mounted on the expandable member of said catheter such that when said configurable segment is moved from said first configuration to said second configuration, all or substantially all of the fastener is oriented at an angle different from the oriented angle in said first configuration.

16. A vascular treatment system as in claim 15 wherein said fastener includes an expanded configuration and said framework includes a longitudinal length and a diameter, said fastener being moveable from said delivery configuration to said expanded configuration such that when said framework is positioned within a vascular graft positioned within a vessel and moved from said delivery configuration to said expanded configuration, said tacking members engage the vascular graft thereby securing it to the vessel.

17. A vascular treatment system as in claim 16 wherein said diameter of said framework is greater than said longitudinal length when said fastener is in said expanded configuration.

18. A vascular treatment system as in claim 17 wherein said diameter is greater than 2 times said longitudinal length.

19. A vascular treatment system as in claim 17 wherein said diameter is greater than 5 times said longitudinal length.

* * * * *